(12) United States Patent
Lopez, III

(10) Patent No.: US 8,291,772 B2
(45) Date of Patent: Oct. 23, 2012

(54) METHOD AND APPARATUS FOR TESTING SHEAR FASTENERS USED IN DOWNHOLE TOOLS

(75) Inventor: Abel Lopez, III, Houston, TX (US)

(73) Assignee: WWN, Ltd., Houston, TX (US)

( * ) Notice: Subject to any disclaimer, the term of this patent is extended or adjusted under 35 U.S.C. 154(b) by 147 days.

(21) Appl. No.: 12/821,597

(22) Filed: Jun. 23, 2010

(65) Prior Publication Data

US 2011/0314927 A1    Dec. 29, 2011

(51) Int. Cl.
*G01N 3/02* (2006.01)
*G01N 3/24* (2006.01)

(52) U.S. Cl. .................. 73/845; 73/860; 73/846; 73/856

(58) Field of Classification Search .................. 73/866, 73/865.9, 152.48, 152.49, 761, 774, 815, 73/816, 841, 845
See application file for complete search history.

(56) References Cited

U.S. PATENT DOCUMENTS

| | | | | |
|---|---|---|---|---|
| 3,559,472 A * | 2/1971 | Thompson | ...................... | 73/841 |
| 3,960,013 A | 6/1976 | Ormond | | |
| 3,994,158 A * | 11/1976 | Weinhold | ........................ | 73/798 |
| 4,864,866 A * | 9/1989 | Hardy et al. | ..................... | 73/831 |
| 6,450,041 B1 * | 9/2002 | Ali | ................................. | 73/856 |
| 7,284,447 B2 * | 10/2007 | Scarborough | ..................... | 73/850 |
| 7,448,279 B2 * | 11/2008 | Brinz et al. | ..................... | 73/841 |
| 7,578,619 B2 | 8/2009 | Nakagawa | | |
| 7,918,410 B2 * | 4/2011 | Muzzio | .......................... | 241/27 |
| 2005/0193829 A1 * | 9/2005 | Brinz et al. | ..................... | 73/794 |
| 2007/0006661 A1 * | 1/2007 | Paddock et al. | ................. | 73/761 |
| 2010/0313672 A1 * | 12/2010 | Dee et al. | ........................ | 73/851 |

OTHER PUBLICATIONS

Model 41, Precision Low Profile Load Cell, Honeywell bulletin, May 2008, 6 Pages.
SATEC™ Series DX and LX Models, High Capacity Universal Testing Systems, Instron bulletin, 2008, 8 Pages.

* cited by examiner

*Primary Examiner* — Lisa Caputo
*Assistant Examiner* — Jonathan Dunlap
(74) *Attorney, Agent, or Firm* — Patterson & Sheridan, LLP

(57) ABSTRACT

A tester for testing a shear fastener includes: a frame; a stationary chuck connected to the frame; a linear guide comprising a slider; a movable chuck connected to the slider; a movable insert fastened to the movable chuck and having a hole for receiving a first portion of the shear fastener; a stationary insert fastened to the stationary chuck and having a hole for receiving a second portion of the shear fastener; a linear actuator for engaging the movable chuck and fracturing the shear fastener; and a load cell for determining force exerted on the shear fastener by the linear actuator.

20 Claims, 4 Drawing Sheets

METHOD AND APPARATUS FOR TESTING SHEAR FASTENERS USED IN DOWNHOLE TOOLS

BACKGROUND OF THE INVENTION

1. Field of the Invention

Embodiments of the present invention generally relate to a method and apparatus for testing shear fasteners used in downhole tools.

2. Description of the Related Art

In order to reduce cost of overall production of oil and gas, oilfield service companies have continually sought ways to employ the most accurate and safe equipment in the field. In addition, cost effective ways of deploying and actuating such devices are continually sought. Many of these devices across a number of competitors use a very similar manner to deploy and actuate these devices: shear fasteners.

Shear fasteners serve a dual purpose, they fasten bodies of a down-hole tool together and they must break at a specified value in order to deploy, set, release, or actuate a tool. Because of this function, the shear fastener must shear perpendicular to its axis at a very precise value of pound force.

In order to procure parts that would be known to shear at a precise value of pound force, oilfield service companies have created a number of proprietary shear testing procedures, shear testing devices, and shear fastener designs. Most of these shear testing devices, or testers, are composed of inner and outer sleeves that move in opposite directions. This opposing motion causes the shear force. When procuring these fasteners, the oil and gas service companies approach suppliers who must manufacture according to a number of different procedures and testers. This approach can be very costly.

Ideally, the testers employed by the oil and gas service companies should mimic the operation of their downhole tools. In this way, the test data would accurately reflect downhole operation of the fasteners. However, existing testers are designed for testing fasteners for several different tools. Consequentially, the testers do not accurately represent any particular downhole tool geometrically or functionally. The tester operates in a laboratory environment, whereas the downhole tools have very long and straight slips which restrict lateral movement. Since these downhole tools are manufactured to be very long, the tolerances in between the bodies that make them up are not exacerbated. In this sense, a shorter tester will exacerbate the loose tolerances between the bodies that make it up, resulting in an inaccurate test result.

Additionally, current designs of testers for general use do not have the ability to test a variety of different fastener configurations in an efficient manner.

SUMMARY OF THE INVENTION

Embodiments of the present invention generally relate to a method and apparatus for testing shear fasteners used in downhole tools. In one embodiment, a tester for testing a shear fastener includes: a frame; a stationary chuck connected to the frame; a linear guide comprising a slider; a movable chuck connected to the slider; a movable insert fastened to the movable chuck and having a hole for receiving a first portion of the shear fastener; a stationary insert fastened to the stationary chuck and having a hole for receiving a second portion of the shear fastener; a linear actuator for engaging the movable chuck and fracturing the shear fastener; and a load cell for determining force exerted on the shear fastener by the linear actuator.

In another embodiment, a method for testing a shear fastener includes: manufacturing the shear fastener; manufacturing inserts specifically for the shear fastener; fastening the inserts into respective chucks of a tester; inserting the shear fastener into the inserts; fracturing the shear fastener using the tester; and recording the fracture force determined by a load cell of the tester.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
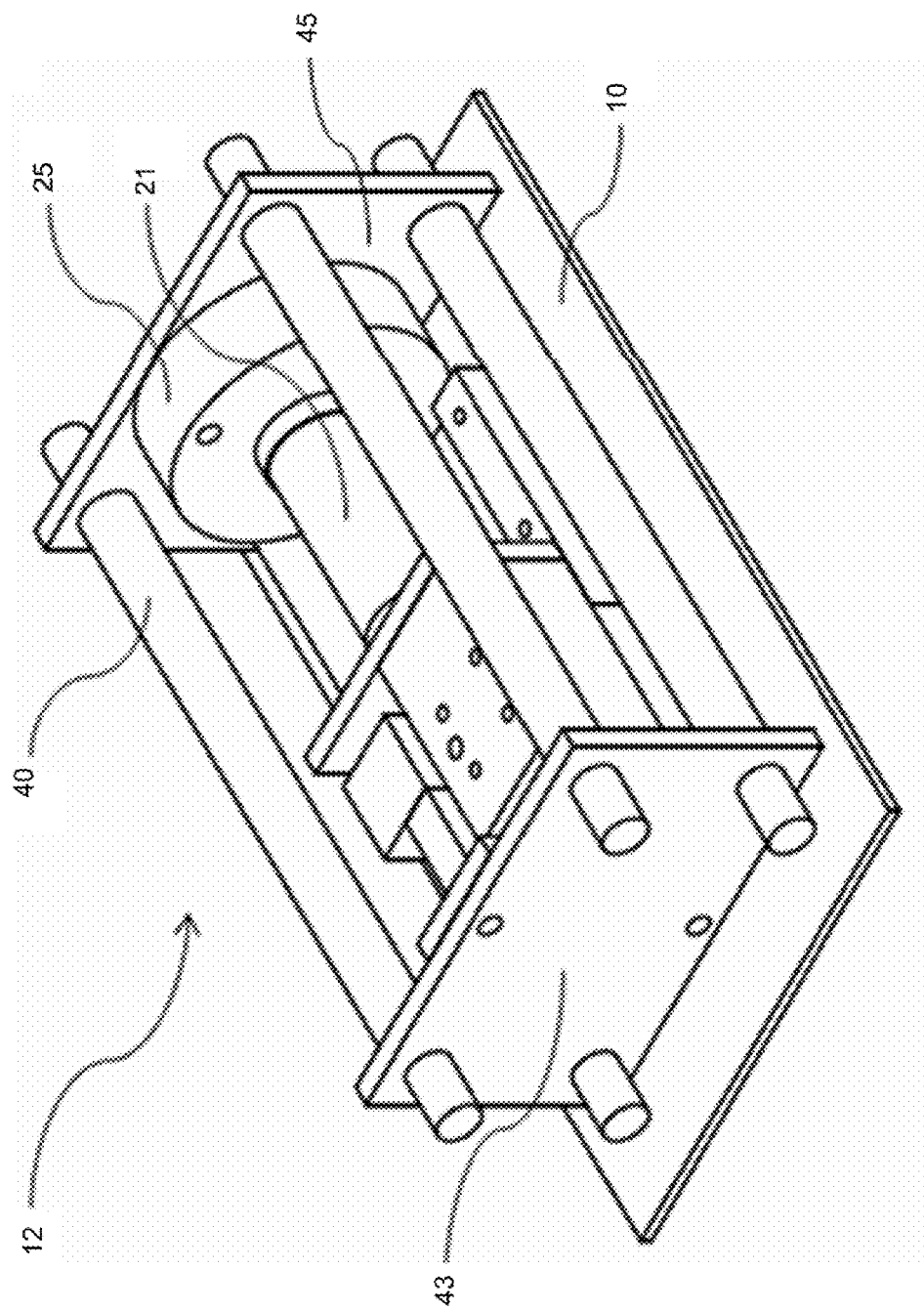
FIG. 1 is an orthogonal view of a shear fastener tester, according to one embodiment of the present invention.

FIG. 1 is an orthogonal view of a shear fastener tester 12, according to one embodiment of the present invention. The tester 12 may be operable to test a variety of shear fastener geometries without needing costly test fixtures. The tester 12 may also simulate the motion of a number of various downhole tools more accurately than prior art shear testers.

The tester 12 may include a frame, a linear actuator, a linear guide, a load cell, and a test fixture. The frame may include a base 10, first 45 and second 43 load plates, and one or more load rods 40, such as four. The frame may be made from a metal or alloy, such as steel or stainless steel. Each load plate 45, 43 may be connected to the base 10, such as by welding or fastening, at or near respective opposing ends of the base 10. Each load rod 40 may extend between each of the load plates 45, 43 and may also extend through openings formed in the plates 45, 43. Each load rod 40 may be connected to each of the plates 45, 43, such as by welding or fastening. A work space may be formed by the base 10, the load rods 40 and the load plates 45, 43, such as a rectangular box (having one or more open sides). The frame may be sufficiently rigid to exhibit minimal or negligible deformation in response to an actuation force exerted by the linear actuator.

Figure 2:
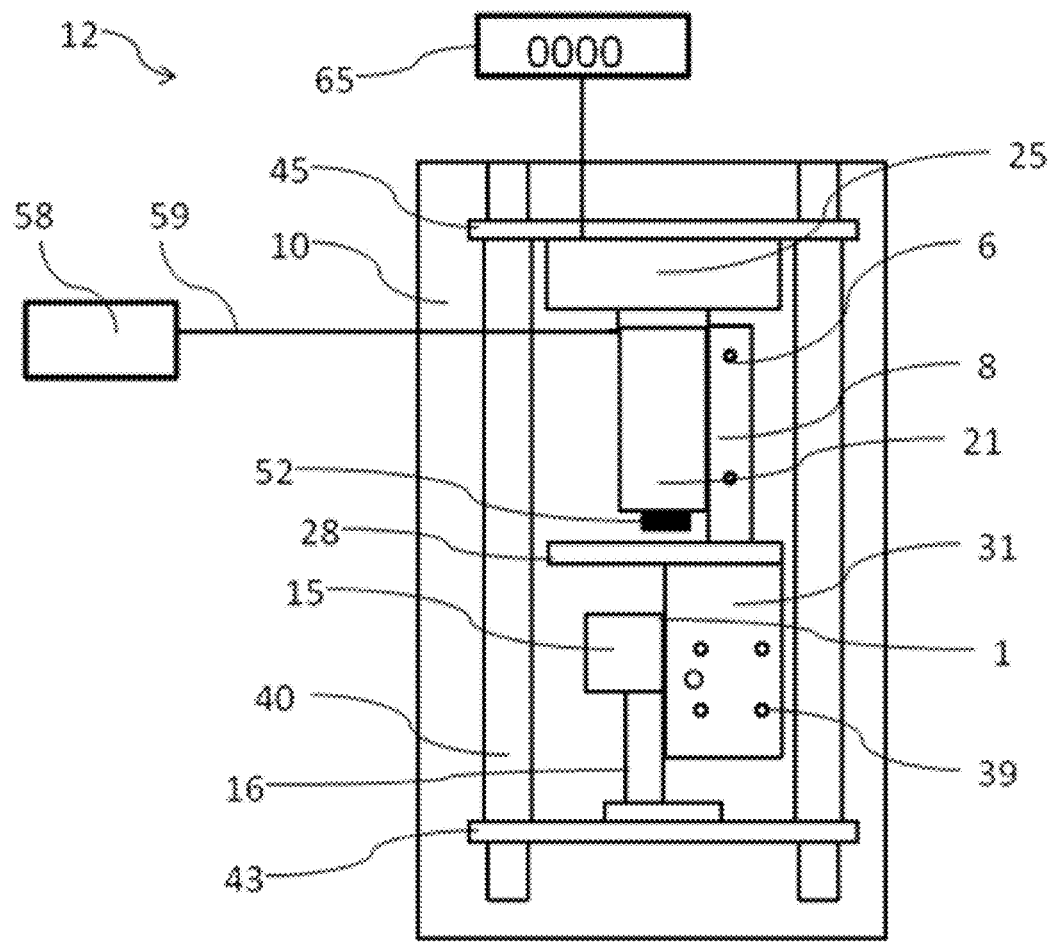
FIG. 2 is a top view of the tester.

FIG. 2 is a top view of the tester 12. The linear actuator may include a pump 58, a cylinder 21, a piston 52, a conduit 59, and a hydraulic fluid reservoir (not shown). The hydraulic fluid may be mineral oil. Alternatively, the linear actuator may include an electric motor and lead screw. The pump 58 may be driven by an electric motor. The pump 58 may be operable to inject hydraulic fluid into the cylinder 21 via the conduit 59, thereby exerting pressure on a first face of the piston 52. The linear actuator may further include a return spring (not shown) biasing the piston 52 toward a retracted position. Exertion of pressure on the first face may extend the piston 52 horizontally from the cylinder 21 and into contact with an adapter 28, such as plate. Alternatively, the linear actuator may include a second conduit in communication with a second face of the piston and the pump may be reversed to retract the piston. The cylinder 21 may be connected to a disc of the load cell 25, such as by fastening. The cylinder 21 may be horizontally oriented.

The load cell 25 may be a pancake type and include a base, the disc, and one or more diaphragms, such as two. The load cell base, disc, and diaphragm may be made from a metal or alloy, such as steel or stainless steel. The base of the load cell 25 may be connected to the first load plate 45, such as by fastening, such that the load cell 25 transfers actuation force from the cylinder 21 to the load plate 45. The disc may have an inner portion, an outer ring, and webs connecting the inner portion and the outer ring. An outer portion of each diaphragm may be connected to the outer ring, such as by welding, and an inner portion of each diaphragm may be connected to the disc inner portion, such as by welding. The disc may be disposed between the two diaphragms and an outer portion of one of the diaphragms may be connected to the base. The diaphragms may serve to transfer side forces and bending moments from the disc to the load cell base, thereby allowing only longitudinal load to be transferred through the web. The load cell base may also house the disc and diaphragms or a cover may be fastened to the base.

One or more strain gages may be disposed on one or more surfaces of one or more of the webs. Each strain gage may be made of a thin foil grid and bonded to the web by a polymer support, such as an epoxy glue. The foil strain gages may be made from a metal or alloy, such as platinum, tungsten/nickel, or chromium. One or more sets of four strain gages may be arranged in a Wheatstone bridge configuration for improved accuracy. The strain gages may be oriented to measure tension or compression of the webs by actuation force from the linear actuator. Alternatively, the strain gages may be made from a piezoelectric, magnetostrictive, or thick film material.

The strain gages may be electrically connected to a data acquisition unit (DAU) 65. The DAU 65 may include a battery or a power cord for plugging into a wall outlet and a display, such as an LCD screen. The DAU 65 may include a rectifier, amplifier, and microprocessor controller. The DAU 65 may output a DC signal to the strain gages. The amplifier may receive the signal from the strain gages, amplify the signal, and feed the signal to the controller. The controller may convert the signal to digital data, calculate the actuation force from the strain data and material and geometric properties of the load cell disc, and display the calculated actuation force on the display. The controller may also include a data port, such as USB or Ethernet, for connection with a server, desktop, or laptop for recording of the shear force data. Alternatively, the load cell 25 may include an internal amplifier or the amplifier may be separate from the DAU.

The test fixture may be made from a metal or alloy, such as steel or stainless steel. The test fixture may include a movable chuck 31, a stationary chuck 15, a movable insert 37, and a stationary insert 30. The frame may further include a bracket 16 connected, such as welded or fastened, to the second load plate 43. The bracket 16 may include two or more structural members, such as rods and plates, connected, such as welded or fastened, together. The stationary chuck 15 may be connected, such as welded or fastened, to the bracket 16. Alternatively, the load cell 25 may instead be connected between the second load plate 43 and the stationary chuck 15. The adapter plate 28 may be connected to the movable shear chuck 31, such as by fastening or welding.

Figure 3:
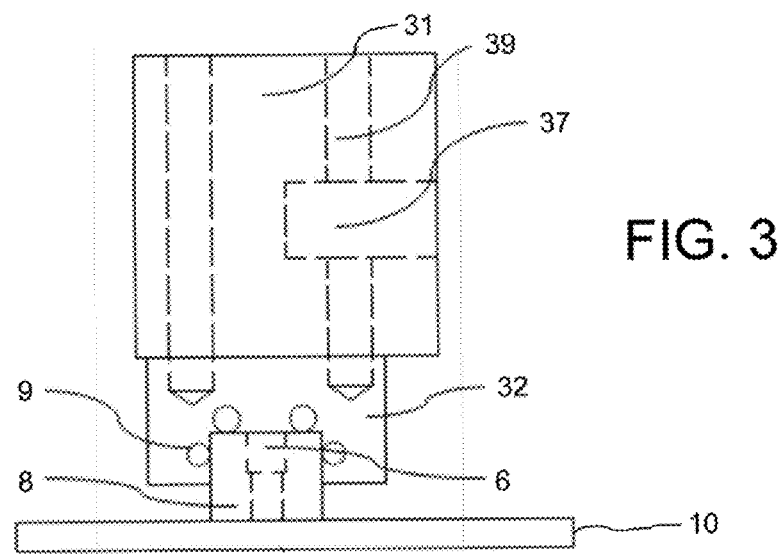
FIG. 3 is a back view of the movable chuck and linear guide.

FIG. 3 is a back view of the movable shear chuck 31 and the linear guide. A suitable linear guide is discussed and illustrated in U.S. Pat. No. 7,568,619, which is herein incorporated by reference in its entirety. The linear guide may include a guide rail 8 extending horizontally along the base 10 and a slider 32 coupled to the guide rail 8 and longitudinally movable relative to the guide rail. The rail 8 may be connected to the base 10, such as by one or more fasteners 6.

The guide rail 8 may have one or more grooves formed in an outer surface thereof and extending therealong. The groves may be formed in each side face of the rail outer surface. A second set of grooves may be formed in upper corners of the rail outer surface and extend therealong. The slider 32 may also have corresponding grooves opposed to the rail grooves formed along an inner surface thereof. The rail and slider grooves may serve as parts of tracks for rolling elements, such as balls 9, disposed between the rail 8 and the slider 32. In order to complete the tracks, internal longitudinal passages may be formed through the slider 32 and end caps having arcuate passages may be fastened to the slider 32, thereby providing a continuous path for the balls 9. As the slider 32 moves relative to the rail 8, the balls 9 may roll continuously along the tracks, thereby facilitating relative longitudinal movement between the rail 8 and the slider 32 and preventing lateral and vertical movement of the slider relative to the rail. To facilitate rolling of the balls 9, lubricant, such as grease, may be disposed within the tracks. To contain the lubricant, one or more seals may be connected to the slider 32 and engage the rail 8. The rail 8, slider 32, and balls 9 may be made from a metal or alloy, such as steel or stainless steel. The lubricant seals may be made from a polymer, such as an elastomer.

The movable chuck 31 may be connected to the slider 32, such as by one or more fasteners 39. One or more of the fasteners 39 may also be used to connect the movable insert 37 to the movable chuck 31. The movable insert 37 may also be received in a recess formed in the movable chuck. Alternatively, the movable insert 37 may have a threaded outer surface received by a threaded inner surface of the recess. The stationary insert 30 may be connected to the stationary chuck in a manner similar to the connection between the movable insert and the movable chuck.

Figure 4A:
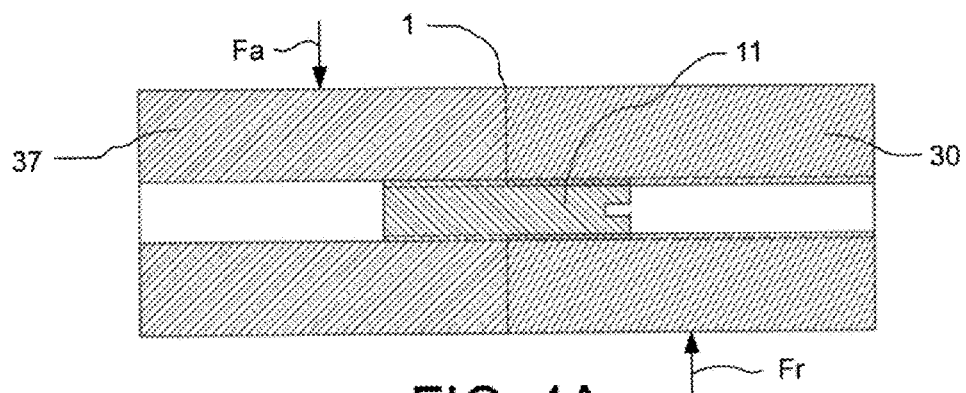
FIGS. 4A and 4B illustrate operation of the tester.
Figure 4B:
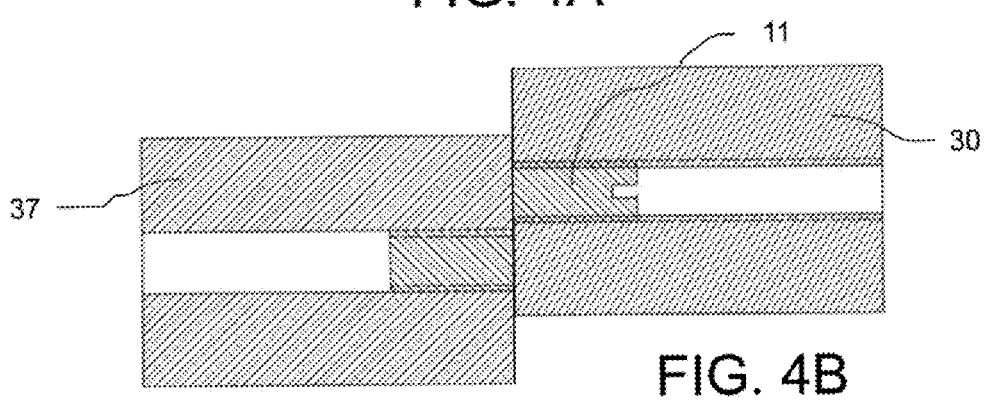

FIGS. 4A and 4B illustrate operation of the tester 12. Each of the inserts 30, 37 may have a hole formed therethrough for receiving a specimen 11, such as a shear fastener (i.e., shear screw). If the specimen 11 is a screw, then one of the holes may be threaded for connection of the specimen 11 and one of the holes may be smooth. Alternatively, both of the holes may be threaded. Alternatively, the hole may only extend partially through one of the inserts 30, 37 so that the specimen 11 may contact an end of the hole. One of the chucks 15, 31 may also have a hole formed therethrough for insertion of the specimen 11. If the specimen 11 is not threaded, such as a pin, then the pin may be press fit or shrunk fit in one of the inserts 30, 37.

Once the specimen 11 is inserted and connected to the inserts 30, 37, the pump 58 may be operated to extend the piston 52 into engagement with the adapter 28. Once the piston 52 contacts the adapter 28, the piston 52 may continue to push the movable chuck 31 along the rail 8 and exert an actuation force $F_a$ on the adapter 28 which may be transferred through the movable chuck 31 to the movable shear insert 37 and onto a first portion, such as a half, of the specimen 11. The stationary insert 30 may restrain a second portion, such as a half, of the specimen 11, thereby exerting a reaction force $F_r$ on the specimen. The reaction force $F_r$ may then be transferred to the stationary chuck 15, the bracket 16, and into the second load plate 43. The plane 1 of shear may be the point at which the force reverses and where the specimen 11 fractures. As the specimen 11 is sheared, the DAU 65 may monitor the actuation force $F_a$ (calculated from output by the load cell 25)

until the specimen 11 fractures. The DAU 65 may then display the fracture force (i.e., maximum $F_a$).

The location of the force arrows $F_a$, $F_r$ are for illustration purposes only. The piston (centerline) 52 may be aligned with the shear plane 1 to obviate any bending moment that may otherwise be exerted on the specimen 11. The bracket (centerline) 16 may be substantially aligned with the shear plane 1 and the bracket and stationary chuck 15 may possess sufficient stiffness to transfer any bending moment directly from the stationary chuck 15, through the bracket 16, and to the second load plate 43 without passing through the specimen 11. Alternatively, the piston 52 may be aligned with the bracket 16.

Alternatively, the specimen 11 may have a threaded portion and a smooth portion and either of the portions may be in the shear plane 1.

The inserts 30, 37 may be manufactured to test specimens 11 from a particular lot or batch of shear fasteners in order to emulate downhole conditions for the particular fasteners. Once a specimen 11 from a particular lot has been tested, the tester 1 may be outfitted for the next lot by simply replacing the inserts 30, 37 with inserts manufactured specifically for the next lot. Each set of inserts 30, 37 may be made from standard bar stock, such as one inch by one inch bar. The bar stock may be a metal or alloy, such as steel or stainless steel. In this manner, a supply of blanks, such as one and a half inch length, of the stock may be kept in inventory. The movable and stationary inserts 30, 37 may also be made from the same blanks. This on demand customization results in cost savings over prior art carousel fixtures which attempt to fit all types of specimens into one of several pre-made sockets and which must be replaced if one of the sockets becomes worn. This on demand customization also results in improved accuracy due to flexibility in design of the inserts 30, 37.

Figure 5:
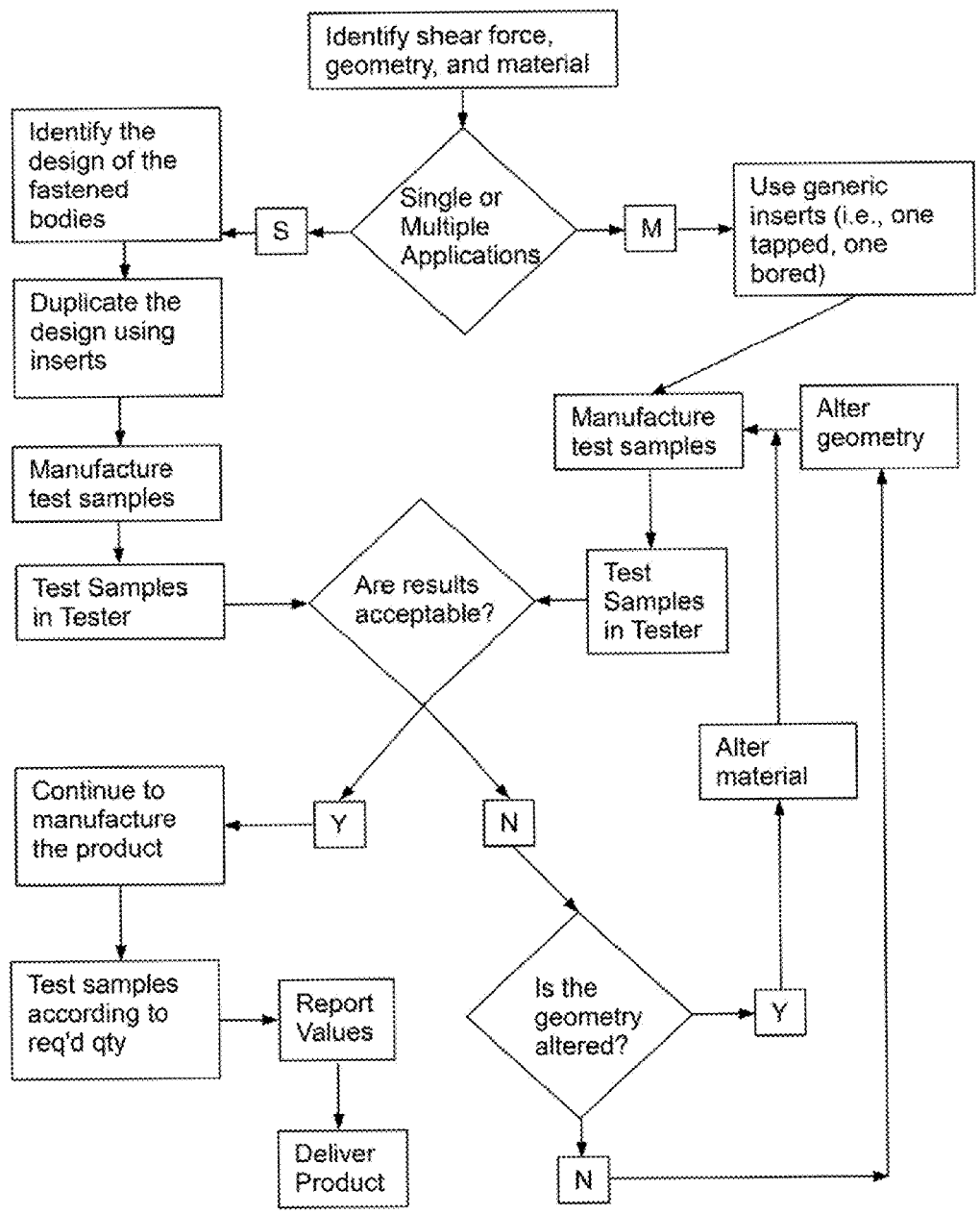
FIG. 5 illustrates a method of designing and testing a shear fastener, according to another embodiment of the present invention

FIG. 5 illustrates a method of designing and testing a shear fastener 11, according to another embodiment of the present invention. A customer may specify acceptable ranges of geometry and fracture force of shear fasteners for a particular downhole tool. The customer may also specify a material class, such as plain carbon steel, low alloy steel, stainless steel, or corrosion resistant alloy (i.e., nickel based alloy). A specific geometry and grade of alloy may be selected (within the customer's specified range and class) to respond at an acceptable fracture force. The customer may also provide design data for the particular downhole tool so that the inserts 30, 37 may be designed to simulate the customer's particular downhole tool. One or more specimens 11 may be made. The specimens 11 may then be tested in the tester 12. The fracture force may be obtained from the tester 12 and compared to the customer's specifications. If the initial specimens 11 fail, the geometry and/or material may be altered and new specimens 11 made. The new specimens 11 may then be tested using the tester 12 and the results compared to the customer's specifications. The alteration of the geometry and/or material may be repeated until the specimens 11 meet the customer's specifications. If the geometry is altered substantially, then new inserts 30, 37 may be made to suit the new geometry. Once the specimens 11 pass, then a batch or lot of shear fasteners may be manufactured and specimens 11 from the lot tested to control quality. The batch or lot may then be delivered to the customer.

Alternatively, the customer may select shear fasteners from a catalog of existing designs. Generic inserts may be maintained in inventory according to the catalog. A lot or batch of fasteners may be made according to the customer's selection in the catalog and specimens 11 from the batch or lot may be tested to ensure the lot conforms to the values specified in the catalog. Alternatively, a new design of shear fastener for the catalog may be tested using the tester 12 to determine the range of fracture force for the catalog.

While the foregoing is directed to embodiments of the present invention, other and further embodiments of the invention may be devised without departing from the basic scope thereof, and the scope thereof is determined by the claims that follow.

The invention claimed is:

1. A tester for testing a shear fastener, comprising:
   a frame;
   a stationary chuck connected to the frame;
   a linear guide comprising a slider;
   a movable chuck connected to the slider;
   a movable insert fastened to the movable chuck and having a hole for receiving a first portion of the shear fastener, wherein the hole is at least partially located in the movable chuck;
   a stationary insert fastened to the stationary chuck and having a hole for receiving a second portion of the shear fastener;
   a linear actuator for engaging the movable chuck and fracturing the shear fastener; and
   a load cell for determining force exerted on the shear fastener by the linear actuator.

2. The tester of claim 1, wherein the linear actuator comprises a piston, cylinder, and a hydraulic pump.

3. The tester of claim 1, wherein the inserts are made from bar stock.

4. The tester of claim 1, wherein the hole of at least one of the inserts is threaded.

5. The tester of claim 4, wherein the hole of at least one of the inserts is smooth.

6. The tester of claim 4, wherein the holes of both inserts are threaded.

7. The tester of claim 1, wherein the tester consists of the two inserts.

8. The tester of claim 1, wherein the actuator is aligned with a shear plane formed between the inserts.

9. The tester of claim 1, wherein:
   the linear guide further comprises a rail connected to the frame, and
   the slider is longitudinally movable along the rail.

10. The tester of claim 9, wherein the rail includes one or more grooves on an outer surface, and the slider has corresponding grooves opposed to the one or more grooves of the rail.

11. The tester of claim 10, wherein at least one rolling element is disposed between the rail and the slider.

12. The tester of claim 1, wherein the frame comprises:
   a base;
   load plates connected to the base at or near ends of the base;
   load rods, each load rod connected to the load plates; and
   a work space formed by the base, load plates, and load rods, wherein the chucks, guide, actuator, and load cell are disposed in the work space.

13. A method for testing a shear fastener using a tester, comprising:
   fastening a first insert to a movable chuck and fastening a second insert to a stationary chuck;
   inserting the shear fastener into the first insert, wherein at least a portion of the shear fastener is located within the movable chuck; fastening the movable chuck to a slider
   fracturing the shear fastener using the tester; and
   recording a fracture force determined by a load cell of the tester.

14. The method of claim 13, further comprising designing the inserts to emulate a specific downhole tool.

15. The method of claim 13, further comprising fastening the shear fastener to at least one of the inserts.

16. The method of claim 13, further comprising:
comparing the fracture force to a specified range;
altering a material and/or geometry of the shear fastener;
manufacturing an altered shear fastener;
fracturing the altered shear fastener using the tester;
recording a fracture force of the altered shear fastener; and
comparing the fracture force of the altered shear fastener to the specified range.

17. The method of claim 13, further comprising:
manufacturing a second shear fastener;
manufacturing second inserts specifically for the second shear fastener;
fastening the second inserts into the respective chucks;
inserting the second shear fastener into the second inserts;
fracturing the second shear fastener using the tester; and
recording a second fracture force determined by the load cell of the tester.

18. A shear fastener manufactured according to the method of claim 13.

19. The method of claim 13, further comprising:
fastening a rail to a frame; and
longitudinally moving the slider along the rail.

20. The method of claim 13, further comprising:
manufacturing the first insert and the second insert specifically for the shear fastener.

* * * * *